US010835584B2

(12) United States Patent
Clapp

(10) Patent No.: US 10,835,584 B2
(45) Date of Patent: Nov. 17, 2020

(54) SYSTEMS FOR TREATING DERMAL INFLAMMATORY CONDITIONS

(71) Applicant: Nuvothera, Inc., Colleyville, TX (US)

(72) Inventor: Arthur Clapp, Colleyville, TX (US)

(73) Assignee: Nuvothera, Inc., Colleyville, TX (US)

( * ) Notice: Subject to any disclaimer, the term of this patent is extended or adjusted under 35 U.S.C. 154(b) by 0 days.

(21) Appl. No.: 15/625,781

(22) Filed: Jun. 16, 2017

(65) Prior Publication Data
US 2017/0360903 A1 Dec. 21, 2017

Related U.S. Application Data

(60) Provisional application No. 62/351,429, filed on Jun. 17, 2016, provisional application No. 62/436,548, filed on Dec. 20, 2016.

(51) Int. Cl.
A61K 38/48 (2006.01)
A61K 33/00 (2006.01)
A61K 31/12 (2006.01)
A61K 9/06 (2006.01)
A61K 31/14 (2006.01)
A61K 31/60 (2006.01)
A61K 9/00 (2006.01)
A61K 31/08 (2006.01)

(52) U.S. Cl.
CPC ........ *A61K 38/4873* (2013.01); *A61K 9/0014* (2013.01); *A61K 9/06* (2013.01); *A61K 31/08* (2013.01); *A61K 31/12* (2013.01); *A61K 31/14* (2013.01); *A61K 31/60* (2013.01); *A61K 33/00* (2013.01); *C12Y 304/22032* (2013.01); *C12Y 304/22033* (2013.01)

(58) Field of Classification Search
None
See application file for complete search history.

(56) References Cited

U.S. PATENT DOCUMENTS

| | | | | |
|---|---|---|---|---|
| 5,110,814 A | * | 5/1992 | Engel | A61K 31/55 514/217.05 |
| 5,925,376 A | | 7/1999 | Heng | |
| 7,556,818 B1 | | 7/2009 | Heng | |
| 2003/0092675 A1 | * | 5/2003 | Duggan | A61K 8/671 514/63 |
| 2003/0113388 A1 | * | 6/2003 | Phan | A61K 8/365 424/756 |
| 2008/0255224 A1 | * | 10/2008 | Blum | A61K 31/352 514/454 |
| 2015/0056272 A1 | * | 2/2015 | Karageozian | A01N 59/00 424/450 |
| 2015/0238576 A1 | * | 8/2015 | Richon | A61K 38/4873 424/94.65 |

FOREIGN PATENT DOCUMENTS

| | | | |
|---|---|---|---|
| GB | 2307176 | * | 5/1997 |
| WO | WO1999042094 A1 | | 8/1999 |
| WO | WO 2006/054312 | * | 5/2006 |

OTHER PUBLICATIONS

Heng et al., Br. J. Dermatol. 143: 937-949 (2000).*
Sullivan et al., Food Chem. Toxicol. 72: 40-50 (2014).*
Sarafian et al., Iranian J. Pharmaceut. Res. 14(3): 865-876 (2015).*
Parnell, Laura, Protein degradation and protection observed in the presence of novel wound dressing components, Journal of Functional Biomaterials, 2011, 2(4), 338-354.
Christophers E. Psoriasis—epidemiology and clinical spectrum. Clinical and experimental dermatology 2001;26:314-20.
Menter A, Gottlieb A, Feldman SR, Van Voorhees AS, Leonardi CL, Gordon KB et al. Guidelines of care for the management of psoriasis and psoriatic arthritis: Section 1. Overview of psoriasis and guidelines of care for the treatment of psoriasis with biologics. J Am Acad Dermatol 2008;58:826-50.
Aggarwal BB , Harikumar KB. Potential therapeutic effects of curcumin, the anti-inflammatory agent, against neurodegenerative, cardiovascular, pulmonary, metabolic, autoimmune and neoplastic diseases. The international journal of biochemistry & cell biology 2009;41:40-59.
Aggarwal BB, Gupta SC , Sung B. Curcumin: an orally bioavailable blocker of TNF and other pro-inflammatory biomarkers. British journal of pharmacology 2013;169:1672-92.
Singh S , Aggarwal BB. Activation of transcription factor NF-kappa B is suppressed by curcumin (diferuloylmethane) [corrected]. The Journal of biological chemistry 1995;270:24995-5000.
Tonnesen HH, de Vries H, Karlsen J , Beijersbergen van Henegouwen G. Studies on curcumin and curcuminoids. IX: Investigation of the photobiological activity of curcumin using bacterial indicator systems. Journal of pharmaceutical sciences 1987;76:371-3.
Bosman B. Testing of lipoxygenase inhibitors, cyclooxygenase inhibitors, drugs with immunomodulating properties and some reference antipsoriatic drugs in the modified mouse tail test, an animal model of psoriasis. Skin pharmacology : the official journal of the Skin Pharmacology Society 1994;7:324-34.
Pol A, Bergers M , Schalkwijk J. Comparison of antiproliferative effects of experimental and established antipsoriatic drugs on human keratinocytes, using a simple 96-well-plate assay. In vitro cellular & developmental biology Animal 2003;39:36-42.
Cho JW, Lee KS , Kim CW. Curcumin attenuates the expression of IL-1beta, IL-6, and TNF-alpha as well as cyclin E in TNF-alpha-treated HaCaT cells; NF-kappaB and MAPKs as potential upstream targets. International journal of molecular medicine 2007;19:469-74.
Sun J, Han J, Zhao Y, Zhu Q , Hu J. Curcumin induces apoptosis in tumor necrosis factor-alpha-treated HaCaT cells. International immunopharmacology 2012;13:170-4.
Heng MC, Song MK, Harker J , Heng MK. Drug-induced suppression of phosphorylase kinase activity correlates with resolution of psoriasis as assessed by clinical, histological and immunohistochemical parameters. The British journal of Dermatology 2000;143:937-49.

(Continued)

*Primary Examiner* — Erin M. Bowers

(57) ABSTRACT

The present invention is directed to novel systems and methods for treating dermal inflammatory disorders, such as psoriasis.

13 Claims, No Drawings

(56) References Cited

OTHER PUBLICATIONS

Kurd SK, Smith N, VanVoorhees A, Troxel AB, Badmaev V, Seykora JT et al. Oral curcumin in the treatment of moderate to severe psoriasis vulgaris: A prospective clinical trial. Journal of the American Academy of Dermatology 2008;58:625-31.
Pavan et al., Properties and Therapeutic Application of Bromelain: A Review, Biotechnol Res Int. 2012; 2012: 976203.
Hsiang-Ping Lee et al., Curcumin induces cell apoptosis in human chondrosarcoma through extrinsic death receptor pathway: International Immunopharmacology 13 (2012) 163-169.
Schon and Boehncke; Psoriasis; New England Journal of Medicine; 352; 18 (2005); 1899-1912.
Zhang et al., Curcumin's Metabolites,Tetrahydrocurcumin and Octahydrocurcumin, Possess Superior Anti-inflammatory Effects in vivo Through Suppression of TAK1-NF-kB Pathway, Frontiers in Pharmacology, 2018, vol. 9 Article 1181, pp. 1-12.

* cited by examiner

SYSTEMS FOR TREATING DERMAL INFLAMMATORY CONDITIONS

CROSS-REFERENCE

This application claims the benefit of U.S. provisional application Nos. 62/351,429 filed Jun. 17, 2016, and 62/436,548, filed Dec. 20, 2016, which applications are incorporated herein by reference.

STATEMENT REGARDING FEDERALLY FUNDED RESEARCH

None.

REFERENCE TO SEQUENCE LISTING

None.

BACKGROUND

Field of the Invention

The present invention relates generally to the fields of compositions and methods for treating dermal inflammatory conditions, such as, but not limited to psoriasis.

Dermal inflammatory conditions are prevalent and cause considerable discomfort and can have significant psychosocial impact for numerous patients. While some treatments include expensive medications requiring prescriptions, many of these can cause long term topical or systemic side effects that limit their use, or they are ineffective and too expensive for many patients in need.

SUMMARY

In one embodiment, principles of the present disclosure provide a system for treating dermal inflammation said system comprising an anti-microbial gel, a treatment gel comprising curcumin and a moisturizer comprising bromelain. In some embodiments, each of said anti-microbial gel, treatment gel and moisturizer are in separate containers. In some embodiments the treatment gel comprises curcumin, bromelain and a pharmaceutically acceptable carrier for topical application. In some embodiments the system further comprises an anhydrous formulation of salicylic acid.

In one embodiment principles of the present disclosure provide a method of treating psoriasis comprising applying a composition of the system described above, comprising an anti-microbial gel comprising at least sodium chlorite, a treatment gel comprising at least turmeric or curcumin, and a moisturizer comprising at least bromelain to the skin of a patient in need thereof. In some embodiments the antimicrobial gel comprises sodium chlorite and optionally may contain benzalkonium chloride. In some embodiments the treatment gel contains salicylic acid and curcumin. In some embodiments coal tar is contained in the treatment gel.

It is contemplated that any embodiment of a method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION

Skin wounds, psoriasis, acne, burns, eczema, and smoking-induced injury are important pathological conditions. Psoriasis is a chronic, immune-mediated, genetic skin disease affecting up to 2% of the world's population[1]. Approximately 80% of patients have mild-to-moderate plaque psoriasis while 20% have moderate-to-severe disease[2]. Mild-to-moderate plaque psoriasis is typically managed with topical therapies, while the more severe forms of plaque psoriasis require phototherapy, oral systemic therapies, or biological agents. Currently available oral systemic therapies include methotrexate, cyclosporine, acitretin, and apremilast, while biological therapies include anti-TNF-α, anti-IL-12/23p40, and anti-IL-17A agents.

These conditions are frequently accompanied by inflammation, which can be mediated by a number of inflammatory cytokines secreted by inflammatory cells such as lymphocytes, macrophages, and dendritic cells and by a number of locally or regionally acting substances, such as histamine, bradykinin, serotonin, the prostaglandins, thromboxanes, leukotrienes, and platelet-activating factor. Thus, while current methods of psoriasis treatment are effective, there exists a need in the art for improved therapeutic compositions and methods having improved safety and producing reduced recurrence rates. Accordingly, the present disclosure provides novel compositions and methods for treating dermal inflammatory conditions such as psoriasis.

By "dermal inflammatory conditions" is meant any condition in which the epidermis or underlying tissue exhibits conditions of inflammation. Such conditions include certain skin wounds, acne, rosacea, burns, eczema, atopic dermatitis, contact dermatitis, seborrheic dermatitis, psoriasis and the like.

Other conditions that may be treated by the novel compositions disclosed herein include pruritus, prurigo nodularis, pityriasis lichenoides, neutrophilic disorders, pyoderma gangrenosum, Sweets Syndrome, granulomatous diseases, sarcoidosis, bullous disorders, papulosquamous disorders, lichen planus, actinic keratosis, warts, pigmentation disorders, post inflammatory hyperpigmentation, scars, dry skin, xerosis, keratosis pilaris, and skin conditions associated with aging, purpura, impaired wound healing, decubitis ulcers, and fibrotic skin conditions, fungal, viral and bacterial skin conditions, diabetic neuropathy, and the like. Also included are veterinary conditions such as wound healing, allergic skin disorders, fungal and bacterial skin disorders, fibrotic skin conditions and the like.

To accomplish treatment of these conditions the present disclosure provides novel systems or kits. These systems include a variety of individual components that when combined provide for beneficial and improved treatment of dermal inflammatory conditions.

A first component of the system is a treatment gel. This component comprises active anti-inflammatory active ingredients including a turmeric extract comprising turmeric, curcumin and/or other curcuminoids and a variety of anti-inflammatory non-curcuminoids including diarylheptanoids, diarylpentanoids, phenylpropenes, phenylpropenes, monoterpenes, sesquiterpenes, diterpenes, triterpenes, sterols and alkaloids. In addition, the treatment gel comprises a topical carrier. In some embodiments cyclodextrin is used in the treatment gel. In some embodiments coal tar is used in the treatment gel. In some embodiments the concentration in the formulation may be from 0.05% to 5.0%. In some embodiments coal tar is found in the treatment gel at a final concentration of around 1% w/v. In some embodiments the treatment gel comprises curcumin, and bromelain and a topical carrier. In some embodiments salicylic acid or bromelain may be used in the treatment gel but may alternatively or in addition be used in other components of the system. In some embodiments the treatment gel comprises turmeric and curcuminoids.

Anti-TNF-α therapies have become the mainstay of systemic therapy for both psoriasis and psoriatic arthritis. Curcuminoids, such as curcumin, demethoxycurcumin, and bisdemethoxycurcumin, and metabolites thereof are components of the spice turmeric and have been recommended for a number of medical applications[3]. Research has suggested curcuminoids can suppress the production of TNF-α from macrophages[4]. It is also been shown that activation of NF-κB can be down-modulated by curcumin[5] and this down-regulation of NF-κB plays a major role in TNF-α suppression. Over 60 clinical trials have evaluated the safety and efficacy of curcumin in humans plus another 35 clinical trials are further evaluating its efficacy[4]. Curcumin has been found to be effective in TNF-α-associated human diseases, such as rheumatoid arthritis, Crohn's disease, and psoriasis. There are several reasons to believe that curcumin or curcuminoids may have potential for treating psoriasis, including its phototoxic effects[6], its anti-psoriatic activity in the modified mouse tail test[7], its inhibition of the proliferation of human keratinocytes through suppression of pro-inflammatory pathways[8, 9], and its ability to reverse the anti-apoptotic function of TNF-α in skin cells[10]. Furthermore, it has shown potentially promising results in two human studies of psoriasis[11, 12]. However, the present disclosure for the first time provides for the use of turmeric, curcumin and/or curcuminoids and or metabolites or variants thereof in combination with bromelain for topical treatment of dermal inflammatory disorders.

Curcuminoids may be obtained from or found in a turmeric extract or may be synthesized as is known in the art and used as a purified synthesized product. In some embodiments, curcuminoids may be hydrogenated. In some embodiments the curcuminoids may be tetrahydrocurcuminoids, hexahydrocurcuminoids and octahydrocurcuminoids, or combinations thereof. In some embodiments curcuminoid modifications include methylation, demethylation, and/or hydrogenation or dehydrogenation and the like.

Sources of curcuminoids are readily available. Curcumin may be added to the composition as a purified compound having the formula of Structure 1 (enol form) or 2 (keto form) or salts, or variants thereof. Alternatively, curcuminoids obtained from a turmeric extract may be added to the compositions disclosed herein. In this embodiment curcuminoid such as curcumin, demethoxycurcumin, and/or bisdemethoxycurcumin, and variants or metabolites thereof, and other bioactive agents, such as, but not limited to polyphenols, terpenes and isoflavones may be included in the compositions disclosed herein. In addition, the treatment gel may contain butylene glycol, caprylolyl glycine, salicylic acid and/or citric acid. Other components may include disodium EDTA, hydroxyethyl acrylate/sodium acryloyldimethyl taurate copolymer, oleth-3 phosphate, PEG-7 trimethylolpropane coconut ether, polyacrylate crossploymer-6, phenoxyethanol, potassium sorbate, cyclodextrin, polyisobutene, sodium bisulfite, sodium hydroxide, tocopheryl acetate, transcutol CG, and/or undecylenoyl glycine. In some embodiments curcumin may be in a nano or nanoemulsified form as disclosed in US20120052095, which is expressly incorporated herein by reference.

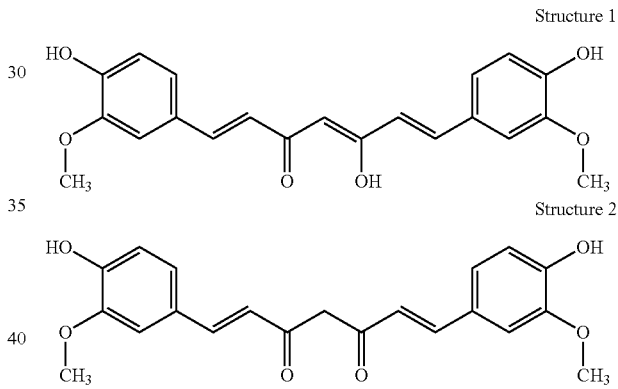

Structure 1

Structure 2

While the prior art has indicated that the use of curcuminoids at a final concentration of greater than 0.1% is required to observe effects, the present disclosure provides for the use of curcumin at a final concentration of less than 0.1%. In one embodiment curcuminoids are used at a final concentration of 0.001% to less than 0.1%. In one embodiment curcuminoids are used at a final concentration of 0.005% to around 0.075%. In one embodiment curcumin is used at final concentration of 0.01 to around to around 0.05%. In one embodiment curcuminoids are used at a final concentration of around 0.05%. In some embodiments hydrogenated curcuminoids, such as but not limited to tetrahydrocurcumin may be used at a concentration of from 0.01 up to 2% w/v. In some embodiments the concentration is from about 0.05% up to about 1.5%. In some embodiments the concentration is from about 0.1% up to about 1% w/v.

When turmeric extract, and/or curcuminoids such as hydrogenated curcumin is used as the source of curcuminoids, the ingredient may be at a final concentration of 0.1% to 10%. In one embodiment the ingredient may be at a final concentration of 0.5 to 5% or from 1% to 2%.

Another component of the treatment gel or moisturizer described herein may be bromelain. That is, in some embodiments bromelain is found in the treatment gel. In alternative embodiments bromelain is found in the moisturizer. Bromelain is a crude extract from the pineapple that contains, among other components, various closely related proteinases, demonstrating, in vitro and in vivo, anti-edematous, anti-inflammatory, keratolytic, anti-pruritic, antithrombotic, and fibrinolytic activities. The active factors involved are biochemically characterized only in part. While bromelain has been used in oral formulations, little is known about is effects following topical application to the skin. However, the present disclosure provides that bromelain in combination with turmeric extracts containing turmeric or curcumin provides for effective treatments of dermal inflammatory conditions, such as psoriasis, to reduce inflammation, reduce scaling, maintain remissions and control itch. While bromelain may be isolated from pineapple, it is commercially available from a number of sources.

In one embodiment therefore, the anti-inflammatory compositions described herein contain bromelain at a final concentration of 0.1% to 10%. w/v. In one embodiment the final concentration of bromelain is from 0.25% to 2% w/v. In one embodiment the final concentration of bromelain is from 0.5% to 1% w/v.

In addition, other therapeutic ingredients that find use in the composition include cortisones, vitamins, green tea catechins, salicylic acid, Coal Tar, lidocaine and other painkillers or anti-inflammatory molecules. These may optionally be found in the treatment gel, moisturizer and/or antimicrobial gel as needed. In some embodiments, salicylic acid is used in the treatment gel and is found at a concentration of about 0.01% to about 3%, in some embodiments from about 0.05% to about 1%, or in some embodiments about 0.5%, all concentrations above w/v. In some embodiments it has been found that salicylic acid used at these concentrations in a substantially anhydrous formulation provides surprisingly beneficial effects. In some embodiments anhydrous salicylic acid formulation or ointment is a separate component from the others described herein. In some embodiments salicylic acid may be used at a concentration of about 0.025%-3% w/v or from 0.05-2% w/v or from 0.075% to 1.5% w/v or from 0.1% to 1% w/v or from 0.25% to 3% w/v or from 0.5% to 2% w/v. Benefits of using salicylic acid include but are not limited to removing scaling and preparing the skin for improved penetration of other ingredients into deeper layers of the skin. Without being bound by theory it is thought that this improves the efficacy of the other ingredients. In some embodiments this formulation produces a low pH after initial contact with the natural low level of moisture in the skin to effectively remove the scaling of the psoriasis patient's skin. The treatment may be used daily, multiple times daily, weekly, bi-weekly as needed and may be used at the same time as the other products contained in the system or applied as an individual treatment. This anhydrous treatment may be applied at night while other components of the system are applied during the day.

By "substantially anhydrous" is meant less than about 5% aqueous solution. Such a formulation may be achieved by methods known in the art, such as but not limited to the use of gels, petrolatum and the like.

A second component of the system disclosed herein is an antimicrobial gel. The anti-microbial gel acts to kill bacteria, viruses and fungus that live on the skin that can trigger inflammatory flares. The anti-microbial gel contains benzalkonium chloride and sodium chlorite, which have a direct anti-inflammatory effect on dermal inflammatory skin conditions. The anti-microbial gel has been shown to reduce odor, reduce inflammation, reduce itching, reduce pain, reduce redness and reduce psoriasis plaques and scaling. It has also demonstrated improvements in the symptoms of eczema, insect bites and stings. In one embodiment it is applied as a leave-on gel. In some embodiments the benzalkonium chloride is found in the antimicrobial gel at a final concentration of around 0.01% to 5% w/v. In some embodiments the final concentration is around 0.1% or around 1%. Other ingredients that find use in the antimicrobial gel include disodium EDTA, PVP, sodium bicarbonate, sodium chlorite, and/or sodium hydroxide.

A third component of the system is a moisturizer. The moisturizer may comprise bromelain and optionally may also comprise salicylic acid and/or glycolic acid and/or lactic acid. In some embodiments salicylic acid is used at a concentration from about 0.5% to about 5%, alternatively from about 1% to about 3%, alternatively from about 1.5% to about 2% w/v. In some embodiments the concentration of salicylic is about 0.5%, about 1%, about 1.5%, about 2%, about 2.5%, or about 3%, all w/v. In some embodiments glycolic acid or lactic acid is used at a concentration of from about 1% to about 15%, alternatively from about 2% to about 12%, alternatively from about 3% to about 10%, alternatively from about 4% to about 8%. In some embodiments, glycolic acid or lactic acid is used at a concentration of about 1%, about 2%, about 3%, about 4%, about 5%, about 6%, about 7%, about 8%, about 9%, about 10%, about 11%, about 12%, about 13%, about 14%, or about 15%, all w/v. In some embodiments curcuminoids and/or hydrogenated curcuminoids may be found in the moisturizer. In addition, the moisturizer may include ammonium lactate or a similar emollient moisturizer. By "emollient moisturizer" is meant an agent that softens and smoothens the scales of the skin, which help reduce rough, flaky skin. In one embodiment the moisturizer may include a humectant occlusive moisturizer. By "humectant moisturizer" is meant an agent that bonds with water molecules to increase the water content in the skin itself. Non-limiting examples of humectant moisturizing agents include hyaluronic acid, glycerin, propylene glycol, urea, allantoin and glycerol. In some embodiments the moisturizer contains an occlusive agent. By "occlusive agent" is meant a substance that provides a layer of protection that helps prevent moisture (water) loss from the skin. Non-limiting examples of occlusive agents include lanolin, petrolatum, mineral oil, sweet almond oil, cetyl alcohol, ceramides and stearyl alcohol. In some embodiments vitamins, such as Vitamin A or D may be included in the moisturizing treatment. In some embodiments, curcuminoids may be added to the moisturizing treatment. In some embodiments indigo may be added to the moisturizing treatment. In some embodiments strontium or calcium salts may be added to the moisturizing treatment. Other components of the moisturizer include butylene glycol, hyaluronic acid, sodium bisulfite, disodium EDTA, transcutol, bromelain, curcumin, hydrogenated curcumin, cyclopentasiloxane, isopropyl palmitate, octyl stearate, petrolatum, tocopheryl acetate, oleth-3 phosphate, phenoxyethanol, potassium sorbate, sodium hydroxide, citric acid, cetyl alcohol, hydroxyethyl acrylate/sodium acryloyldimethyl taurate copolymer, caprylic capric triglycerides, polyisobutene, urea, allantoin, mineral oil, paraffin wax, PEG-7 trimethylol propane coconut ether, polyacrylate crosspolymer-6, undecylenoyl glycine and/or capryloyl glycine.

Compositions of the present disclosure also contain pharmaceutically acceptable carriers. Conventional pharmaceutically acceptable carriers known in the art can include alcohols, e.g., ethyl alcohol, serum proteins, hyaluronic acid, human serum albumin, emu oil, micelles, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, ethoxydiglycol, hydroxyethylacrylate/sodium acryloyldimethyl taurate copolymer, butylene glycol, chelating agents, such as but not limited to EDTA (disodium EDTA), sodium bisulfate, phenoxyethanol, capryloyl glycine, undecylenoyl glycine, oleth-3 phosphate, polyisobutene, PEG-7 trimethylolpropane coconut ether, sorbitan isostearate, sodium hydroxide and the like. A pharmaceutically-acceptable carrier within the scope of the present invention meets industry standards for sterility, isotonicity, stability, and non-pyrogenicity. In some embodiments the composition contains transcutol. In some embodiment the composition contains a gelling agent. In some embodiments the composition contains transcutol. In some embodiments the composition contains aloe.

Once made, the compositions find use in treating dermal inflammatory disorders as described herein. For instance, in a method of treatment one would apply components of the system described herein to the affected area of the skin as needed. In some embodiments each of the system components on a regular and similar basis, while in other embodiments the frequency of application of each of the components may be administered to the affected area of the skin independently of treatment frequency of other system components. That is, in some embodiments each component is applied daily, twice daily, every other day, once a week, twice a week, twice a month, three times a month, monthly, and the like. In other embodiments, each system component is individually applied to the affected area of the skin on an independent schedule. In some embodiments, the components are applied to the affected area of the skin and left on the skin. In some embodiments the components are applied during the day or some may be applied at night.

In some embodiments different components of the system are used at different times and intervals. In one embodiment each of the antimicrobial gel, treatment gel and moisturizer are applied in the morning. In one embodiment in addition to usage in the morning, the the anhydrous ointment comprising salicylic acid may be used at night for the first 2-3 weeks. In this embodiment the anhydrous ointment preferably contains anhydrous salicylic acid. Without being bound by theory, the nightly use of the anhydrous ointment is thought to boost the efficacy of the system and speed the onset and clearing of skin scaling. The result of this regimen is rapid clearing of scaling, and effective reduction and clearing of plaque thickness, redness, itching, pain, skin cracks associated with psoriasis. This regimen helps clear the psoriasis and helps reduce recurrences to help keep skin clear.

In some embodiments the system also includes a micro-derma roller. As is known in the art, micro-derma rollers comprise multiple micro needles on a roller. The roller is rolled across the skin to make multiple minute wounds. Without being bound by theory it is thought that formation of these small wounds stimulates the production of cellular growth factors and collagen growth. Micro-derma rollers come with needles of different length. For instance, in some embodiments, the needle used on the micro-derma roller described herein is from about 0.25 to 3.00 mm in length. For use herein, preferred length are about 0.25 mm, or about 0.5 mm or about 0.75 mm or about 1 mm, or about 1.5 mm or about 2 mm. In some embodiments the needle length is from about 0.15 mm to about 2 mm, or from about 0.2 mm to about 1 mm or from about 0.25 mm to about 0.5 mm. As used herein, the micro-derma roller is rolled over the treatment area to improve skin penetration of ingredients and improve the healing time of the skin lesions, e.g. psoriasis lesions. In some embodiments the micro-derma roller roughens the skin without penetrating the dermis to create a healing response in the skin. The micro-derma roller improves healing time by stimulating growth factors in the skin and stimulating collagen production. The micro-derma roller may be used daily, every other day, bi-weekly or weekly.

This system has been shown to reduce itching and pain associated with psoriasis plaques and it has been shown to reduce redness, plaque thickness, heal cracks in skin, control odor, rejuvenate skin, soften skin, hydrate skin, moisturize skin, clear psoriasis lesions and maintain remission of psoriasis symptoms when used regularly. It improves scalp psoriasis, clearing skin flaking, reducing itching and redness. It has also been shown to reduce the itch often associated with eczema and reduce the associated inflammation and redness. Accordingly, the present disclosure also provides methods of preventing recurrence of dermal inflammatory disorders such as psoriasis. This topical formulation system can be used concomitantly with other prescription and non-prescription psoriasis treatments such as, topical vitamin D preparations, topical steroids, topical or oral retinoids, oral immune-modulating agents or injectable biological agents, PUVA and UV light treatments, coal tar preparations, and the like.

The system is described above including different components in different configurations. In some embodiments the system includes salicylic acid ointment, a psoriasis treatment gel and a therapeutic moisturizer as described herein. In some embodiments the system includes a micro-derma roller, treatment gel and therapeutic moisturizer. In some embodiments the system includes salicylic acid ointment, micro-derma roller, treatment gel and therapeutic moisturizer. In some embodiments the system includes the antimicrobial gel, treatment gel, moisturizer, dermal roller and the anhydrous salicylic acid ointment.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Plaque psoriasis—Older aged male with multiple plaque locations applied the 3-step treatment regimen daily for 3 months. Itching was resolved within minutes of the first application. The redness of the lesions began improving by the second week with improvements in scaling and lesion area by week four through week 8. Lesions were virtually clear by month 3.

Inverse psoriasis—Middle aged male with inverse psoriasis in multiple intregenous areas applied the 3-step treatment regimen for 6 weeks. During that period, itching cleared the first day, redness began improving in the first week and clearing of all sites occurred by week 6.

Eczema—Older aged male with eczema in the groin area applied the 3-step treatment regimen for 2 weeks to the affected area. Rapid improvement of itching occurred during the first hour of treatment including anal itching. Inflammation and eczema symptoms resolved by the end of the first week of treatment. In addition, the same patient reported he was allergic to deodorants and applied the 3-step treatment regimen to the underarm area in an attempt to control body odor. The 3-step treatment regimen completely controlled the subject's body odor during the first application and it was well tolerated. The product was used daily with excellent results.

Example 2

Psoriasis—Middle aged male with chronic psoriasis symptoms stopped topical psoriasis treatment 3 weeks prior. Psoriasis symptoms were becoming significant. Person applied the psoriasis formulation alone and psoriasis plaques cleared in 3 weeks and maintained clear with regular use. Currently has been clear for over 5 months with very little steroid spot treatment or no steroid use. Person has never been virtually free of psoriasis symptoms for this long of duration. Usually experiencing psoriasis symptoms monthly. A formulation of curcumin and bromelain was used. These results were achieved at a curcumin concentration of 0.05% and a bromelain concentration of less than 1%.

Example 3

Chronic Pruritus—Middle aged male reported chronic itching symptoms on the chest for several years. Applied to area of chronic itching. Itching resolved in minutes. This was the first time the patient has been itch free for years. Applied the formulation for a few days and itching cleared for several weeks. A formulation of curcumin and bromelain was used. These results were achieved at a curcumin concentration of 0.05% and a bromelain concentration of less than 1%.

Example 4

Psoriasis—Middle aged male with chronic psoriasis was treated with a psoriasis gel containing turmeric extract in a salicylic acid base or a coal tar base that was applied daily under occlusive patch for 19 days. The person's scaling was completely clear in less than one week using an anhydrous moisturizer pre-treatment containing 0.5% salicylic acid. The person received twice weekly applications of a 0.25 mm derma-roller over the treatment site. The person achieved complete clearing of their psoriasis symptoms with improved skin texture and appearance in 19 days under occlusion using both turmeric containing formulations. Remarkably, at least one treatment patch site still remains clear of psoriasis compared to surrounding untreated plaque after 6 months of ending the study.

Psoriasis—Middle aged male with moderate to severe plaque psoriasis was treated with the 3-product treatment system after failing a course of injectable biological TNF alfa treatment and experiencing severe side effects. Subject demonstrated rapid clearance of scaling in one week. Itching and pain improved in the first week. Skin cracking improved over 3 weeks. Plaque thickness and redness subsided during next 3 months with virtually complete clearing in 5 months. Subject continues to remain clear of psoriasis plaques with continued treatment and now wears shorts in public for the first time in many years.

Psoriasis—Middle aged female with moderate plaque psoriasis was treated with the 3-product treatment system after stopping injectable biological IL-23 treatment when their health insurance would no longer provide reimbursement coverage of the expensive biological. Subject demonstrated rapid clearance of scaling in one week and saw significant reductions in redness and plaque thickness in 2 months. Itching and pain subsided in the first week. Subject's psoriasis plaques were healed by month three with only minor pinkness of skin remaining. Psoriasis lesions were no longer raised compared to nearby normal skin. The subject experienced continuous improvement over 3 months and subject remains virtually clear of psoriasis plaques with continued use.

Psoriasis—Nine subjects with mild to moderate plaque psoriasis participated in a 6-week clinical study using the 3-system psoriasis treatment system. Subjects showed statistically significant improvements in IGA scores at week 2 and week 6. Of the 9 subjects completing the study, 8 subjects (88.9%) demonstrated improvement compared to baseline. By week 6 there was a statistical improvement in scaling, dermal irritation and total symptom score. There was a numerical improvement in erythema and plaque thickness by week 6. Although there was clinical improvement, plaque thickness and erythema typically takes the longest to resolve. The subjects rated the products after 6 weeks of use and 100% reported Products feel nice on skin, Products are not greasy, Products are easy to use, Products spread easily, Products do not have a bad smell, I like the products, I would like to continue using the products.

REFERENCES

1. Christophers E. Psoriasis—epidemiology and clinical spectrum. Clinical and experimental dermatology 2001; 26:314-20.
2. Menter A, Gottlieb A, Feldman S R, Van Voorhees A S, Leonardi C L, Gordon K B et al. Guidelines of care for the management of psoriasis and psoriatic arthritis: Section 1. Overview of psoriasis and guidelines of care for the treatment of psoriasis with biologics. J Am Acad Dermatol 2008; 58:826-50.
3. Aggarwal B B, Harikumar K B. Potential therapeutic effects of curcumin, the anti-inflammatory agent, against neurodegenerative, cardiovascular, pulmonary, metabolic, autoimmune and neoplastic diseases. The international journal of biochemistry & cell biology 2009; 41:40-59.

4. Aggarwal B B, Gupta S C, Sung B. Curcumin: an orally bioavailable blocker of TNF and other pro-inflammatory biomarkers. British journal of pharmacology 2013; 169: 1672-92.

5. Singh S, Aggarwal B B. Activation of transcription factor NF-kappa B is suppressed by curcumin (diferuloylmethane) [corrected]. The Journal of biological chemistry 1995; 270:24995-5000.

6. Tonnesen H H, de Vries H, Karlsen J, Beijersbergen van Henegouwen G. Studies on curcumin and curcuminoids. IX: Investigation of the photobiological activity of curcumin using bacterial indicator systems. Journal of pharmaceutical sciences 1987; 76:371-3.

7. Bosman B. Testing of lipoxygenase inhibitors, cyclooxygenase inhibitors, drugs with immunomodulating properties and some reference antipsoriatic drugs in the modified mouse tail test, an animal model of psoriasis. Skin pharmacology: the official journal of the Skin Pharmacology Society 1994; 7:324-34.

8. Pol A, Bergers M, Schalkwijk J. Comparison of antiproliferative effects of experimental and established antipsoriatic drugs on human keratinocytes, using a simple 96-well-plate assay. In vitro cellular & developmental biology Animal 2003; 39:36-42.

9. Cho J W, Lee K S, Kim C W. Curcumin attenuates the expression of IL-1beta, IL-6, and TNF-alpha as well as cyclin E in TNF-alpha-treated HaCaT cells; NF-kappaB and MAPKs as potential upstream targets. International journal of molecular medicine 2007; 19:469-74.

10. Sun J, Han J, Zhao Y, Zhu Q, Hu J. Curcumin induces apoptosis in tumor necrosis factor-alpha-treated HaCaT cells. International immunopharmacology 2012; 13:170-4.

11. Heng M C, Song M K, Harker J, Heng M K. Drug-induced suppression of phosphorylase kinase activity correlates with resolution of psoriasis as assessed by clinical, histological and immunohistochemical parameters. The British journal of dermatology 2000; 143:937-49.

12. Kurd S K, Smith N, VanVoorhees A, Troxel A B, Badmaev V, Seykora J T et al. Oral curcumin in the treatment of moderate to severe psoriasis vulgaris: A prospective clinical trial. Journal of the American Academy of Dermatology 2008; 58:625-31.

The invention claimed is:

1. A system for treating dermal inflammation said system comprising:
   a. an anti-microbial gel comprising sodium chlorite and PVP;
   b. a treatment gel comprising 0.01% to 2% tetrahydrocurcumin, a turmeric extract comprising curcuminoids, and about 0.01% to about 3% salicylic acid, wherein said treatment gel lacks curcumin; and
   c. a moisturizer comprising bromelain.

2. The system according to claim 1 wherein each of said anti-microbial gel, treatment gel and moisturizer are in separate containers.

3. The system according to claim 1, wherein said anti-microbial gel further comprises benzalkonium chloride.

4. The system according to claim 3, wherein the final concentration of bromelain in said moisturizer is 0.1% to 10%.

5. The system according to claim 1 wherein at least one of said anti-microbial gel, treatment gel or moisturizer comprises a pharmaceutically acceptable carrier for topical application.

6. The system according to claim 5, wherein the pharmaceutically acceptable carrier comprises transcutol and a gelling agent.

7. A method of treating dermal inflammation of a patient comprising applying the anti-microbial gel, treatment gel and moisturizing cream of the system according to claim 1 to the skin of a patient in need thereof, whereby dermal inflammation of said patient is reduced.

8. A method of treating psoriasis comprising applying the anti-microbial gel, treatment gel and moisturizing cream of the system according to claim 1 to the skin of a patient in need thereof.

9. The system according to claim 1, wherein said treatment gel further comprises cyclodextrin.

10. A system for treating dermal inflammation said system comprising:
   a. an anti-microbial gel comprising sodium chlorite, PVP and benzalkonium chloride;
   b. a treatment gel comprising:
      i. 0.01% to 2% tetrahydrocurcumin;
      ii. a turmeric extract comprising curcuminoids;
      iii. about 0.01% to about 3% substantially anhydrous salicylic acid; and
      iv. cyclodextrin; wherein said treatment gel lacks curcumin;
   c. a moisturizer comprising bromelain; and
   d. an anhydrous ointment comprising 0.025%-3% w/v salicylic acid.

11. The system according to claim 1, further comprising:
   d. an anhydrous ointment comprising 0.025%-3% w/v salicylic acid.

12. The system according to claim 1, wherein at least one of said curcuminoids is selected from the group consisting of demethoxycurcumin, and bisdemethoxycurcumin.

13. The system according to claim 10, wherein at least one of said curcuminoids is selected from the group consisting of demethoxycurcumin, and bisdemethoxycurcumin.

* * * * *